United States Patent
McMaster

(10) Patent No.: US 10,058,543 B2
(45) Date of Patent: Aug. 28, 2018

(54) TREATMENT OF FAMILIAL EXUDATIVE VITREORETINOPATHY THROUGH S1PR2 INHIBITION

(71) Applicant: DALHOUSIE UNIVERSITY, Halifax, Nova Scotia (CA)

(72) Inventor: Christopher McMaster, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 0 days.

(21) Appl. No.: 15/316,072

(22) PCT Filed: Jun. 1, 2015

(86) PCT No.: PCT/CA2015/050503
§ 371 (c)(1),
(2) Date: Dec. 2, 2016

(87) PCT Pub. No.: WO2015/184541
PCT Pub. Date: Dec. 10, 2015

(65) Prior Publication Data
US 2017/0135997 A1   May 18, 2017

Related U.S. Application Data

(60) Provisional application No. 62/006,779, filed on Jun. 2, 2014.

(51) Int. Cl.
*A61K 31/444* (2006.01)

(52) U.S. Cl.
CPC .................. *A61K 31/444* (2013.01)

(58) Field of Classification Search
None
See application file for complete search history.

(56) References Cited

U.S. PATENT DOCUMENTS

| | | |
|---|---|---|
| 2004/0235794 A1 | 11/2004 | Nakade et al. |
| 2006/0148844 A1 | 7/2006 | Nakade et al. |
| 2009/0004207 A1* | 1/2009 | Hla ................. A61K 31/00 424/172.1 |

FOREIGN PATENT DOCUMENTS

| | | |
|---|---|---|
| CA | 2775587 A1 | 4/2011 |
| CA | 2868277 A1 | 10/2013 |
| WO | 01/98301 A1 | 12/2001 |
| WO | 03/051876 A1 | 6/2003 |
| WO | 2008/154470 A1 | 12/2008 |
| WO | 2009/074969 A2 | 6/2009 |
| WO | 2010/030976 A2 | 3/2010 |
| WO | 2011/041287 A1 | 4/2011 |
| WO | 2011/058993 A1 | 5/2011 |
| WO | 2011/084486 A1 | 7/2011 |
| WO | 2011/087051 A1 | 7/2011 |
| WO | 2011/159864 A1 | 12/2011 |
| WO | 2012/164103 A2 | 12/2012 |

OTHER PUBLICATIONS

PCT Search Report and Written Opinion dated Aug. 11, 2016 in PCT Application No. PCT/CA2016/050620, filed on Jun. 1, 2016 to Applicant Dalhousie University, 19 pages.

Sumida, G., et al., "S1P2 receptor Regulation of Sphingosine-1-Phosphate Effects on Conventional Outflow Physiology". American Journal of Physiology—Cell Physiology, Feb. 2, 2011 (Feb. 2, 2011), vol. 300, pp. C1164-C1171, abstract.

Xu, Q. et al., "Vascular Development in the Retina and Inner Ear: Control by Norrin and Frizzled-4, a High-Affinity Ligand-Receptor Pair". Cell, Mar. 19, 2004 (Mar. 19, 2004), vol. 116, pp. 883-895, p. 883, cols. 1 and 2.

Junge, H. et al., "TSPAN12 Regulates Retinal Vascular Development by Promoting Norrin-but not Wnt-Induced FZD4/beta-Catenin Signaling". Cell, Oct. 16, 2009 (Oct. 16, 2009), vol. 139, pp. 299-311, p. 299, cols. 1 and 2.

Okamoto, Y. et al., "Sphingosine-1-Phosphate-Specific G Protein-Coupled Receptors as Novel Therapeutic Targets for Atherosclerosis". Pharmaceuticals, Jan. 4, 2011 (Jan. 4, 2011), vol. 4, pp. 117-137.

PCT Search Report and Written Opinion dated Sep. 3, 2015, for PCT/CA2015/050503, filed Jun. 1, 2015, titled Treatment of Familial Exudative Vitreoretinopathy Through S1PR2 Inhibition, Applicant: Dalhousie University, 12 pages.

Park et al., "Inhibition of Sphingosine 1-Phosphate Receptor 2 Protects against Renal Ischemia-Reperfusion Injury," J Am Soc Nephrol, Feb. 2012, 23(2), pp. 266-280.

Extended European Search Report dated Nov. 21, 2017 in related EP Application No. 15802481.0, filed Dec. 1, 2016 to Dalhousie University, 7 pages.

\* cited by examiner

*Primary Examiner* — Heidi Reese

(74) *Attorney, Agent, or Firm* — Polsinelli PC; Brian McKnight; Ron Galant

(57) ABSTRACT

Methods and compositions are provided for the treatment of familial exudative vitreoretinopathy (FEVR) and retinopathy of prematurity (ROP) through the administration of a therapeutically effective amount of a Sphingosine-1-phosphate receptor type 2 (S1PR2) inhibitor.

4 Claims, 9 Drawing Sheets

A. Normal eye

B. FEVR vascular defect

C. Partial retinal detachment due to FEVR

Wild type

Tspan12$^{-/-}$

Tspan12$^{-/-}$ S1pr2$^{-/-}$ wild type adult zebrafish retina        *fzd4*[-/-] zebrafish retina

TREATMENT OF FAMILIAL EXUDATIVE VITREORETINOPATHY THROUGH S1PR2 INHIBITION

CROSS-REFERENCE TO RELATED APPLICATIONS

This application claims the benefit of Provisional Application Ser. No. 62/006,779 filed Jun. 2, 2014, titled, "TREATMENT OF FAMILIAL EXUDATIVE VITREORETINOPATHY THROUGH S1PR2 INHIBITION", which is herein incorporated by reference in its entirety.

FIELD OF THE TECHNOLOGY

This technology relates generally to methods for treating retinal vascular disorders, and more specifically, treating familial exudative vitroretinopathy (FEVR) and retinopathy of prematurity (ROP) through S1PR2 inhibition.

BACKGROUND

The retina is a thin layer of neural tissue lining the back of the eye responsible for sensing visual stimuli. During development, the retinal vasculature is initiated by endothelial sprouts that lay down the primary arteries and veins that project outward radially from the optic disc to the retinal periphery, with a pair of capillary beds located on either side of the central layer of neurons further penetrating the retina. Patterning of the retinal vasculature is controlled by guidance cues driven initially by tissue hypoxia, which induces a vascular endothelial growth factor (VEGF) gradient sensed by tip cells, specialized endothelial cells at the front end of the growing vasculature. Tip cells migrate along a preexisting astrocyte network with endothelial stalk cells following the tip cells. Once in place, the primary vasculature undergoes maturation to specify arteries and veins, the nascent network is pruned, and the blood-retina barrier is formed. Recruitment of vascular smooth muscle cells and pericytes (also known as mural cells, contractile cells that wrap around endothelial cells of capillaries) aid in stabilization of the newly formed vessels. The molecular mechanisms controlling vessel development in the eye are not well understood.

In humans, retinal vascular development is usually accomplished around term birth but is delayed or arrested in retinal developmental disorders such as familial exudative vitreoretinopthy (FEVR). FEVR is characterized by hypovascularization of the retina due to the failure of peripheral retinal vascularization, followed by secondary aberrant neovascularization. Severe forms of FEVR present with bilateral congenital retinal folds or retinal detachment (FIG. 1). Currently, management of FEVR is by laser and surgery. While interventions improve the chance of retaining vision, more than 75% of eyes remain legally blind despite current best efforts. One study described improvement of retinal hemorrhage and neovascularization after ocular injection with bevacizumab (Avastin, a monoclonal antibody that inhibits VEGF function originally developed to treat cancers) for a FEVR patient, however, the role of anti-VEGF agents in FEVR amelioration remains unclear and has not been widely adopted. Despite current intervention options, loss of vision occurs in the majority of FEVR patients. The idea treatment for this condition would entail early detection with early intervention with a therapy that will prevent the complications from progressing altogether.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

The discovery of genes that, when mutated, cause FEVR has increased the understanding of the molecular pathways that regulate retinal vascular development. To date, five genes have been identified that cause FEVR: FZD4, LRP5, TSPAN12, NDP and ZNF408. Four of the five known FEVR causing genes form a frizzled receptor signaling complex (FIG. 2). FZD4 is part of the frizzled family of seven transmembrane receptors that are normally activated by the Wnt family of ligands. FZD4 is unique among the frizzled receptor family in that it is specifically activated by the non-Wnt ligand norrin, the product of the NDP gene. Norrin is secreted from Müller glial cells and binds to FZD4 receptors located on vascular endothelial cells. LRP5 is a co-receptor for FZD4 and is required for FZD4 to function. TSPAN12 is specifically expressed in endothelial cells, directly binds to FZD4, and enhances the interaction between norrin, FZD4, and LRP5. Like most frizzled receptors, FZD4 signals are transduced via the □-catenin signaling pathway. The translocation of cytosolic □-catenin to the nucleus, where it affects transcription of numerous genes, is the main driving factor behind frizzled receptor signaling (FIG. 2).

Mouse knockout models for Fzd4, Tspan12, Lrp5, and Ndp serve as accurate mimics of the ocular phenotypes observed in FEVR patients. These models have allowed for a detailed analysis of the FEVR phenotype. An important observation from the mouse studies was that, although retinal vasculature is impaired in mouse models of FEVR, the retina itself appears morphologically normal, offering a window of opportunity for intervention that could reverse vision loss due to retinal ischemia.

Having significant phenotypic overlap with FEVR, retinopathy of prematurity (ROP) is a disorder that affects the vasculature of the retina of infants who are born prematurely. Infants with ROP have avascular zones of retina and are at risk of developing secondary aberrant neovascularization and subsequent retinal detachment. Treatment for severe ROP includes laser and bevacizumab. Recent studies suggest current treatments result in 20/40 or better vision in ~⅓ of patients, while ~¼ will be legally blind. Driving vision standards will not be met by ~⅔ of premature babies who develop severe ROP in spite of treatment, and ~50% will be left with severe visual impairment. Although some of the vision loss can be attributed to the neurological complications of prematurity, most vision loss correlates with the status of the retina.

The precise etiology of ROP is currently unknown. However, evidence exists describing a potential molecular link between ROP and FEVR as polymorphisms in FEVR causing genes have been identified in patients with severe ROP. In addition, Fzd4 and Lrp5 expression are downregulated in a rodent ROP model, consistent with a decrease in FZD4 signaling contributing to the ROP phenotype. To further confirm this link and add the first functional data, the extent of vaso-obliteration and subsequent neovascularization in the well-established mouse model of ocular ischemic retinopathy (OIR) used to mimic human ROP was determined, in wild type and Fzd4$^{+/-}$ (heterozygous) mice. Fzd4$^{-/-}$ mice were observed to have defective recovery of angiogenesis following re-exposure to room air compared to wild type mice (FIG. 3). The similar clinical presentation of FEVR and ROP, coupled with links between FEVR causing genes and the severity of ROP, predict that a therapy for FEVR could have efficacy for the treatment of ROP. FEVR treatments may also translate to other retinal vascular disorders such as diabetic retinopathy.

Sphingosine-1-phosphate (S1P) is a blood borne lipid second messenger generated from the metabolism of sphingomyelin through the action of sphingomyelinase, ceramidase, and sphingosine kinase (FIG. 4). The main sites of S1P generation are endothelial cells and erythrocytes. S1P activates the endothelial differentiation family of G protein coupled receptors, named S1PR1-5 (formerly Edg1-5). S1PRs are expressed in different cell types, and regulate numerous biological processes. S1PR1, -2, and -3 function are of particular interest as they are expressed on vascular endothelial cells and regulate vascular development and stability.

S1PR1 is essential for vascular stabilization and increases vascular migration. S1PR1 couples to $G_i$ and activates the phosphatidylinositol 3-kinase pathway, which through Rac affects actin assembly and cell migration. A similar overlapping function has been reported for S1PR3 coupling to $G_q$. In contrast, S1PR2 antagonizes S1PR1 and -3 signaling. S1PR2 primarily activates $G_{12/13}$ and activates the Rho-Rho kinase pathway and inhibits Rac function (FIG. 5). The balance between these antagonizing S1PR pathways determines the endothelial cell response to S1P. To this extent, the inhibition of S1PR2 signaling would provide therapeutic effect for retinal vascular disorders, such as FEVR and ROP, given the important of S1p in retinal vasculature development.

Overall, the screening for S1PR2 inhibitors will lead to the identification of novel approaches for the treatment of retinal vasculature disorders such as FEVR and ROP. The present invention provides for a composition and method that safely and effectively treats individuals suffering from FEVR and SOP through the administration of therapeutically effective amounts of S1PR2 inhibitors.

In a further aspect, the invention provides for a composition and method that safely and effectively treats individuals suffering from generalized retinal vascular disorders, including diabetic retinopathy and macular degeneration.

In a further aspect, the invention provides a kit comprising a pharmaceutical composition comprising S1PR2 inhibitors, which may include small molecules or biologics, and instructions for administering to a subject the composition for treating a subject who is suffering from FEVR or ROP.

As used herein, a "nucleic acid" or a "nucleic acid molecule" means a chain of two or more nucleotides such as RNA (ribonucleic acid) and DNA (deoxyribonucleic acid).

As used herein, the term "inhibition" refers to the reduction of biological activity of a protein, preferably the reduction of activity of the human protein S1PR2.

As used herein, the term "gene" is meant a nucleic acid molecule that codes for a particular protein, or in certain cases, a functional or structural RNA molecule.

As used herein, "protein" and "polypeptide" are used synonymously to mean any peptide-linked chain of amino acids, regardless of length or post-translational modification, e.g., glycosylation or phosphorylation.

When referring to a nucleic acid molecule or polypeptide, the term "wild type" refers to a naturally-occurring (e.g., native, WT) nucleic acid or polypeptide.

As used herein, the terms "treatment" and "therapy" are defined as the application or administration of a therapeutic agent to a patient or subject, or application or administration of the therapeutic agent to an isolated tissue or cell line from a patient or subject, who has a disorder or disease, a symptom of disorder or disease or a predisposition toward a disorder or disease, with the purpose to cure, heal, alleviate, relieve, alter, remedy, ameliorate, improve or affect the disorder or disease, the symptoms of disorder or disease, or the predisposition toward disorder or disease.

The term "therapeutically effective amount", as used herein, means the amount of the S1PR2 inhibitor that will elicit the desired therapeutic effect or response.

The terms "patient," "subject" and "individual" are used interchangeably herein, and mean a mammalian (e.g., human, rodent, non-human primates, canine, bovine, ovine, equine, feline, etc.) subject to be treated, diagnosed, and/or to obtain a biological sample from.

The term "kit" as used herein refers to a packaged product comprising components with which to administer the therapeutically effective amount of the S1PR2 inhibitor for treatment of FEVR and ROP. The kit preferably comprises a box or container that holds the components of the kit. The box or container is affixed with a label or a Food and Drug Administration approved protocol. The box or container holds components of the invention that are preferably contained within plastic, polyethylene, polypropylene, ethylene, or propylene vessels. The vessels can be capped-tubes or bottles. The kit can also include instructions for administering the S1PR2 inhibitor

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
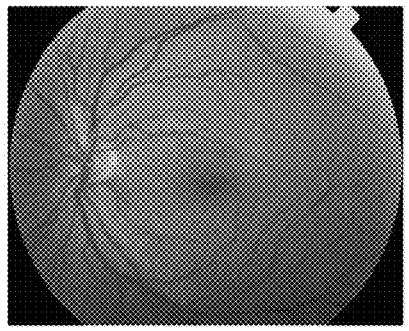
FIG. 1 illustrates vascularization of the human eye. (A) Normally, the retinal vasculature projects outward from the optic disc to the retinal periphery. Familial exudative vitreoretinopathy (FEVR) is an inherited disorder that results in hypovascularization of the retina (B) and subsequent aberrant neovascularization can result in retinal detachment (C).
Figure 1:
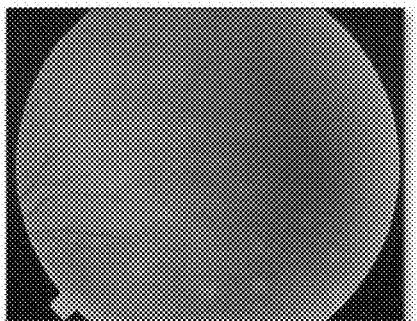
Figure 1:
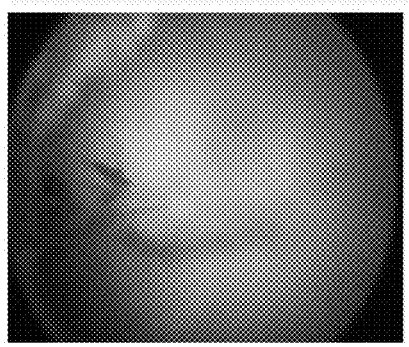
Figure 2:
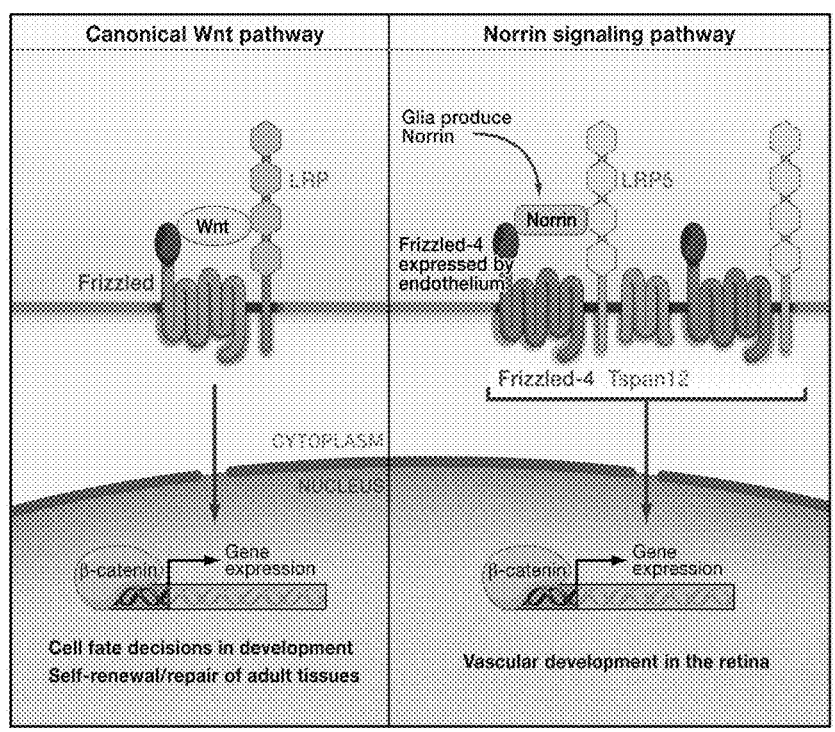
FIG. 2. illustrates the canonical Wnt pathway compared to the Norrin pathway. Norrin signaling through the Frizzled-4 receptor specifically regulates vascular development in the retina. Mutations in the genes encoding for Norrin, Frizzled-4, LRP5, and TSPAN12 cause familial exudative vitreoretinopathy (FEVR). (Fig. from Cell 139, 227-29)
Figure 3:
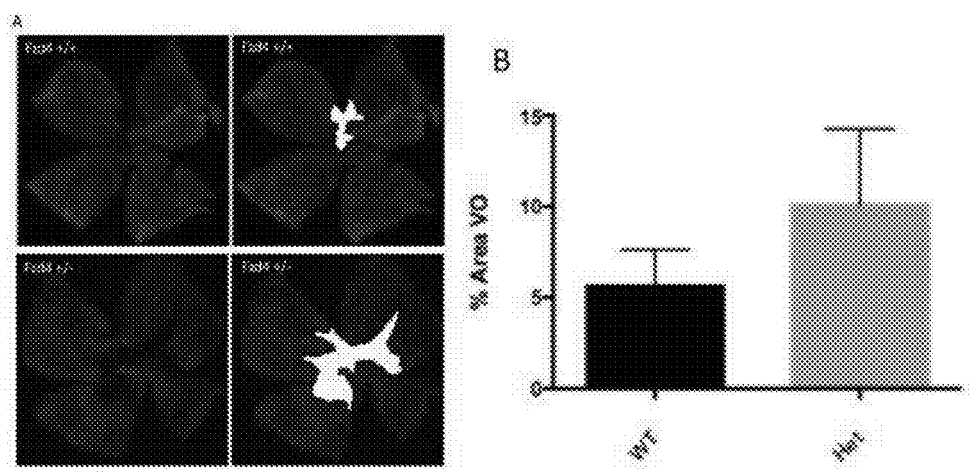
FIG. 3 illustrates vasculature in whole-mounted mouse retinas in Fzd4$^{+/+}$ and Fzd4$^{+/-}$ mice subsequent to a modified ocular ischemic retinopathy model. At P12, upon removal from the oxygen chamber, the area of vaso-obliteration was similar between wild type and Fzd4$^{+/-}$ mice (not shown). At P17, five days after return to room air, whole-mounted retinas were stained with iso-lectin (A), demonstrating that atherogenesis in the Fzd4$^{+/-}$ mice (white area delineates areas that are still vaso-obliterated) is delayed. (B) Quantitation of the area of vaso-obliteration remaining in wild type and Fzd4$^{+/-}$ mice at P17. Mean of eight experiments (p<0.01).
Figure 4:
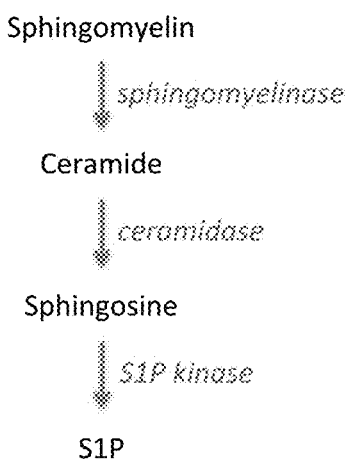
FIG. 4 illustrates that the blood borne second messenger sphingosine-1-phosphate (S1P) is generated in endothelial cells through the sphingomyelinase pathway. S1P can go on to bind a series of five S1P receptors (S1PRs). S1PRs 1, 2, and 3 are found on endothelial cells and regulate vascularization.
Figure 5:
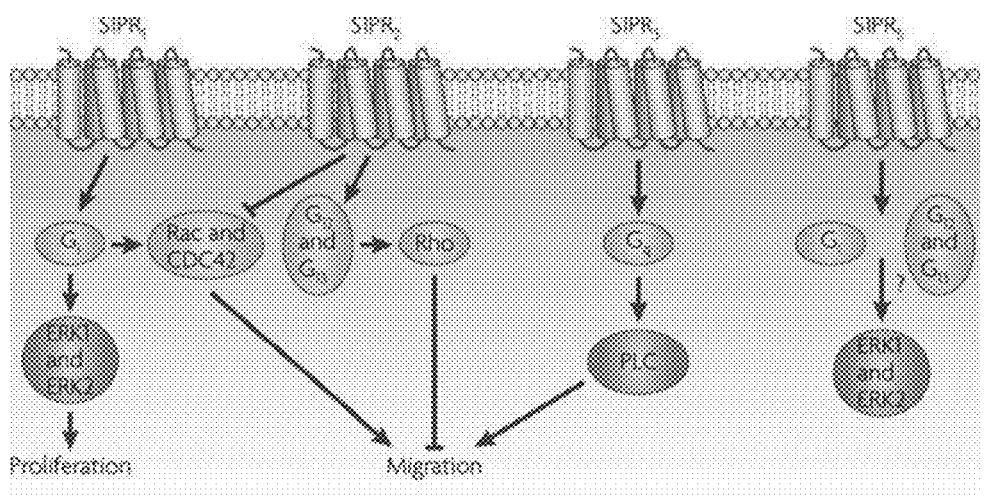
FIG. 5 illustrates sphingosine-1-P receptors (S1PR). S1PR1, 2, and 3 are found on vascular endothelial cells. S1PR1 and S1PR3 drive vascular migration while S1PR2 counteracts their action. To this extent, inhibition of S1PR2 (inhibiting an inhibitor of vascular migration) will result in restoration of normal retinal vascularization for the retinal vascular developmental disorder familial exudative vitreoretinopathy (FEVR). (Fig from Nat. Rev. Cancer 10, 489-503)

Various embodiments of the disclosure are discussed in detail below. While specific implementations are discussed, it should be understood that this is done for illustration purposes only. All references cited within this disclosure are incorporated herein. A person skilled in the relevant art will recognize that other components and configurations may be used without parting from the spirit and scope of the disclosure.

Described are compositions and methods for treating retinal vascular disorders through the administration of therapeutically effective amounts of S1PR2 inhibitors. The treatment regime, in a preferred embodiment, is geared towards the treatment of FEVR and ROP.

In one embodiment, the therapeutically effective amount of the S1PR2 inhibitor has the formula selected from the following group of PubChem identifiers: 3382778; 44317142 (also as 520 and 644260); 54736865; 3866342; 46891770 (also as 3247041); 51624406; 9578291; 9864156; 365015; 28094480; 40592676; 10883396; 342302; 56923845; 54734912; 18390590; 56923928; 51508548; 28960354; 51624683; 27993.

In another embodiment, the S1PR2 inhibitor is the small molecule 1-(2,6-dichloro-4-pyridyl)-3-[(4-isopropyl-1,3-dimethyl-pyrazolo[3,4-n]pyridin-6-yl)amino]urea, with the following chemical structure:

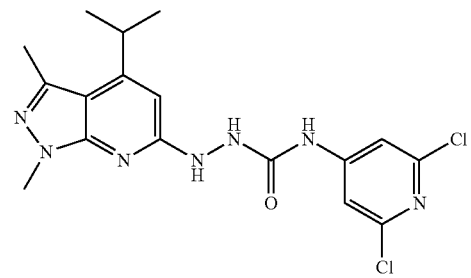 [SMILES: Cc1nn(C)c2nc(NNC(=O)Nc3cc(Cl)nc(Cl)c3)cc(C(C)C)c12]

In another embodiment, the S1PR2 inhibitor is a compound characterized by the general formula:

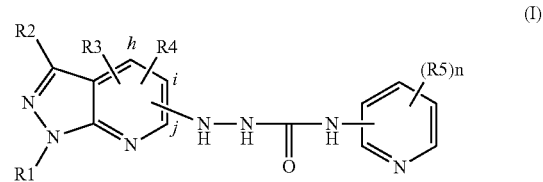

wherein:

R1 is a C1-C12 alkyl, and R2, R3 and R4 are each independently hydrogen, halogen, C1-C6 alkyl, C1-C6 perhaloalkyi, C1-C4 perhaloalkoxy, amino, mono- or di C1-C4 alkylamino, C3-C7 cycloalkyl or C3-C7 cycloalkoxy, and R3 and R4 are optionally positioned at h, i, or j, but not simultaneously at the same position, and R5 is, halogen, C1-C6 alkyl, C1-C6 perhaloalkyi, C1-C4 perhaloalkoxy, amino, mono- or di C1-C4 alkylamino, C3-C7 cycloalkyl or C3-C7 cycloalkoxy, and n is 0, 1, 2, 3 or 4;

2-amino-2-[2-(4-octylphenyl)ethyl]propane-1,3-diol; 5-[[3-chloro-4-(2,3 dihydroxypropoxy)phenyl]methyl]-3-(o-tolyl)-2-(propylamino)thiazolidin-4-one; 2-amino-2-[2-[4-(3-benzyloxyphenyl)sulfanyl-2-chloro-phenyl]ethyl] propane-1,3-diol; 1-[5-[(3R)-3-amino-4-hydroxy-3-methylbutyl]-1-methyl-pyrrol-2-yl]-4-(p-tolyl)butan-1-one;

3-amino-4-(3-octylanilino)-4-oxo-butyl]phosphonic acid; 5-[4-phenyl-5-(trifluoromethyl)-2-thienyl]-3-[3-(trifluoromethyl)^oxadiazole;

or a compound characterized by a general formula II (II)

$$\text{R1} \quad \text{pyrimidine ring with X, R2, W-Q-R substituents}$$

wherein:

X is $NR^aR^b$, $SR^b$, F, Cl, Br or I, and

R1 is H or $R^b$

R2 is H, F, Cl, Br, I, or $R^b$ $R^a$ is H or $R^b$, and $R^b$ is branched or linear alkyl having 1 to 12 carbon atoms, wherein one or more, preferably 1 to 7 hydrogen atoms may be replaced by F, Cl, Br, I, $OR^a$, $COOR^3$, CN, $N(R^a)_2$ and wherein one or more, preferably 1 to 7 non-adjacent CH2-group may be replaced by O, $NR^a$, S or $SO_2$, and/or by —CH=CH— groups, or is cycloalkyl or cycloalkylalkylene having 3 to 7 ring carbon atoms, and W is C=O, C=S, SO2 or SO, and Q is NR3, —O— or —S—, and R is hydrogen, Rb, Ar or Het, and Ar is a monocyclic or bicyclic, saturated, unsaturated or aromatic carbocyclic ring having 6 to 14 carbon atoms which may be unsubstituted, mono-, di-, or tri-substituted by F, Cl, Br, I, $R^b$, OR3, —$[C(R^3)_2]$n-$OR^3$, $N(R^3)_2$, —$[C(R^3)2]$n-$N(R^3)_2$, $NO_2$, CN, $COOR^3$, $CF_3$, $OCF_3$, $CON(R^3)$, $NR^3COA$, $NR^3CON(R^3)_2$, —$[C(R^3)_2]$n-Het, —$[C(R^3)_2]$n-Ar, —$[C(R^3)_2]$n-cycloalkyl, —$[C(R^3)_2]$n-$CON(R^3)_2$, —$[(R^3)_2]$n-$COOR^3$, —$[C(R^3)_2]$n-$NR^3$—$[C(R^3)_2]$n-$CO_2R^3$; —$[C(R^3)_2]$n-$NR^3$—$[C(R^3)_2]$n-$OR^3$, —$SO_2$—$[C(R^3)2]$n-$CO_2R^3$, —$SO_2$—$N(R^3)_2]$n-$[CO_2R^3$, —$[C(R^3)_2]N$—$SO_2$—$[C(R^3)]$n-$CO_2R3$, —SO2$[C(R^3)_2]$n-$OR^3$, —$SO_2N(R^3)_2$—$[C(R^3)_2]$n-$OR^3$, —$[C(R^3)_2]N$—$SO_2$—$[C(R^3)_2]$n-$OR^3$, $NR^3CON(R^3)_2$, $NR^3SO_2R^b$, $COR^3$, $SO_2N(R^3)_2$, SO2N(R3)Rb, SORb, $SONR^3R^b$, $SO_2R^b$, and/or —$O[C(R^3)_2]$n-$COOR^3$ and Het is a monocyclic or bicyclic, saturated, unsaturated or aromatic heterocyclic ring having 1 to 4 N, O and/or S which may be unsubstituted, mono-, di-, or trisubstituted by F, Cl, Br, I, $R^b$, OR3, —$[C(R^3)_2]$n-$OR^3$, $N(R^3)_2$, —$[C(R^3)2]$n-$N(R^3)_2$, $NO_2$, CN, $COOR^3$, $CF_3$, $OCF_3$, $CON(R^3)$, $NR^3COA$, $NR^3CON(R^3)_2$, —$[C(R^3)_2]$n-Het, —$[C(R^3)_2]$n-Ar, —$[C(R^3)_2]$n-cycloalkyl, —$[C(R^3)_2]$n-$CON(R^3)_2$, —$[(R^3)_2]$n-$COOR^3$, —$[C(R^3)_2]$n-$NR^3$—$[C(R^3)_2]$n-$CO_2R^3$; —$[C(R^3)_2]$n-$NR^3$—$[C(R^3)_2]$n-$OR^3$, —$SO_2$—$[C(R^3)2]$n-$CO_2R^3$, —$SO_2$—$N(R^3)_2]$n-$[CO_2R^3$, —$[C(R^3)_2]N$—$SO_2$—$[C(R^3)]$n-$CO_2R3$, —SO2$[C(R^3)_2]$n-$OR^3$, —$SO_2N(R^3)_2$—$[C(R^3)_2]$n-$OR^3$, —$[C(R^3)_2]N$—$SO_2$—$[C(R^3)_2]$n-$OR^3$, $NR^3CON(R^3)_2$, $NR^3SO_2R^b$, $COR^3$, $SO_2N(R^3)_2$, SO2N(R3)Rb, SORb, $SONR^3R^b$, $SO_2R^b$, and/or —$O[C(R^3)_2]$n-$COOR^3$, and $R^1$ is H or Rb, and $R^2$ is H, F, Cl, Br, I, or Rb, and $R^3$ is is H or Rb, and n is 0, 1, 2, 3, 4, 5, 6, 7 or 8;

2-[1-[2-(5-chloro-2,4-dimethoxy-anilino)-2-oxo-ethyl]-2,4-dioxo-quinazolin-3-yl]acetic acid; —N-(5-chloro-2,4-dimethoxy-phenyl)-2-[2,4-dioxo-3-[2-oxo-2-[2-(3-pridyl)ethyl-amino]ethyl]quinazolin-1-yl]; 2-[4-[1-[2-(5-chloro-2,4-dimethoxy-anilino)-2-oxo-ethyl]-2,4-dioxo-quinazolin-3-yl]phenyl]-N-phenethyl-acetamide; 4-[6-chloro-1-[2-(3-chloro-4-ethoxy-phenyl)-2-oxo-ethyl]-2,4-dioxo-quinazolin-3-yl]-N-cyclopentyl-butanamide; N-(5-chloro-2,4-dimethoxy-phenyl)-2-[2,4-dioxo-3-[2-(phenethylamino)ethyl]quinazolin-1-yl]acetamide; -tert-butyl 2-[1-[2-(5-chloro-2,4-dimethoxy-anilino)-2-oxo-ethyl]-2,4-dioxo-quinazolin-3-yl]acetate; -tert-butyl N-[2-[1-[2-(5-chloro-2,4-dimethoxy-anilino)-2-oxo-ethyl]-2,4-dioxo-quinazolin-3-yl]ethyl]carbamate; -2-[1-[2-(5-chloro-2,4-dimethoxy-anilino)-2-oxo-ethyl]-2,4-dioxo-pyrido[3,2-d]pyrimidin-3-yl]acetic acid; -2-[1-[2-(5-chloro-2,4-dimethoxy-anilino)-2-oxo-ethyl]-2-oxo-4H-quinazolin-3-yl acetic acid; N-(5-chloro-2,4-dimethoxy-phenyl)-2-[3-(3-methoxybenzoyl)-7-methyl-4-4a,8a-dihydro-1,8-naphthyridin-1-yl]acetamide; 2-[1-[2-[(2,6-dichloro-4-pyridyl)amino]-2-oxo-ethyl]-5-methyl-2,4-dioxo-quinazolin-3-l]acetic acid; 4-methyl-8-(2,4,6-trimethylanilino)-2H-phthalazin-1-one; 4-methyl-8-(2,4,6-trimethylanilino)-2H-isoquinolin-1-one; 8-(2,6-dimethylanilino)-2H-isoquinolin-1-one; 8-(4-fluoro-2,6-dimethyl-anilino)-4-methyl-2H-phthalazin-1-one; -4-ethyl-8-(2,4,6-trimethylanilino)-2H-phthalazin-1-one; 4-isopropyl-8-(2,4,6-trimethylanilino)-2H-phthalazin-1-one; -4-(2-hydroxyethyl)-8-(2,4,6-trimethylanilino)-2H-phthalazin-1-one; -8-(2,6-diethyl-4-fluro-anilino)-4-methyl-2H-phthalazin-1-one; 8-(4-chloro-2,6-dimethyl-anilino)-4-methyl-2H-phthalazin-1-one; -4-ethyl-8-(4-fluoro-2,6-dimethyl-anilino)-2H-phthalazin-1-one; -5-(2-propylpyrazol-3yl)2-2(2,4,6-trimethylanilino)benzamide; -5-methoxy-2-(2,4,6-trimethylanilino)benzamide; 5-chloro-2-(2,4,6-trimethylanilino)benzamide.

In another embodiment, the S1PR2 inhibitor is a compound with the general formula:

$$Ar^2-X$$
$$----$$
$$Y$$
$$----$$
$$Z-W-Ar^1$$

Wherein:

$Ar^1$ is optionally substituted heterocycle or aromatic heterocycle;

$Ar^2$ is optionally substituted heterocycle or aromatic heterocycle;

W is $NR^a$—, O, or —$CH_2$—, wherein W is hydrogen or $C_1$-$C_3$ alkyl;

Z is —C(=O)—, —C(=S)—, O, —$CH_2$—, =N—, or =CH—;

Y is —$NR^a$—, —C(=O)—, —N=, —CH=, =N—, or =CH—; and

X is —$NR^a$—, —N=, —CH=, or —$CH_2$—.

In another embodiment, the S1PR2 inhibitor is a compound with the general formula:

Formula II $$\text{pyrrole fused ring structure with } R^1, R^2, R^3, R^4, X^2, X^2{}_j, X==Y==Z-W-Ar^1$$

wherein
Ar$^1$ is aromatic heterocycle;
W, Z, Y and X are as previously defined;
R$^1$ is C$_1$-C$_{12}$ alkyl;
R$^2$, R$^3$, and R$^4$ are each independently hydrogen, halogen, C$_1$-C$_6$ alkyl, C$_1$-C$_4$alkoxy, C$_1$-C$_6$ perhaloalkyl, perhaloalkoxy, amino, mono- or di-C$_1$-C$_4$alkylamino, C$_3$-C$_7$cycloalkyl, or C$_3$-C$_7$cycloalkyloxy;
R$^3$ and R$^4$ can be positioned at h, i, or j, but not simultaneously at the same position; and
X$^2$ is N or —CR$^b$— wherein R$^b$ is hydrogen, halogen, C$_1$-C$_6$ alkyl, C$_1$-C$_4$alkoxy, C$_1$-C$_6$ perhaloalkyl, C$_1$-C$_4$ perhaloalkoxy, amino, mono- or di-C$_1$-C$_4$alkylamino, C$_3$-C$_7$cycloalkyl, or C$_3$-C$_7$cycloalkyloxy In another embodiment, the S1PR2 inhibitor is a compound with the general formula:

Formula III wherein
R$^1$ is C$_1$-C$_1$, alkyl;
R$^2$, R$^3$, and R$^4$ are each independently hydrogen, halogen, C$_1$-C$_6$ alkyl, C$_1$-C$_4$alkoxy, C$_1$-C$_6$ perhaloalkyl, C$_1$-C$_4$ perhaloalkoxy, amino, mono- or di-C$_1$-C$_4$alkylamino, C$_3$-C$_7$cycloalkyl, or C$_3$-C$_7$cycloalkyloxy;
each instance of R$^5$ is halogen, C$_1$-C$_6$ alkyl, C$_1$-C$_4$alkoxy, C$_1$-C$_6$ perhaloalkyl, C$_1$-C$_4$ perhaloalkoxy, amino, mono- or di-C$_1$-C$_4$alkylamino, C$_3$-C$_7$cycloalkyl, or C$_3$-C$_7$cycloalkyloxy; and
n is 0, 1, 2, 3, or 4.

In another embodiment, the S1PR2 inhibitor is a compound with the general formula:

Formula I wherein:
A is a direct bond or (CR) and B, C and D are independently selected from the group consisting of (CR) and N, wherein R is H or alkyl, provided however, not all, of B, C and D are N and, when A is a direct bond, D is (CR);
R$^3$ is selected from the group consisting of alkyl;
X is selected from the group consisting of O, NR$^4$ and CR$^4$R$^5$, wherein R$^4$ and R$^5$ are independently selected from the group consisting of H and alkyl;
Y is selected from the group consisting of O or S; and
Z is a substituted aryl ring.

In another embodiment, the S1PR2 inhibitor is a compound with the general formula:

Formula II wherein:
R$^1$ and R$^2$ are independently selected from the group consisting of H and alkyl, methoxy, hydroxyl, halogen, nitrile, and trifluoromethyl;
R$^3$ is independently selected from the group consisting of alkyl, methoxy, hydroxyl, halogen, nitrile, and trifluoromethyl;
D is CR or N;
R is H or alkyl;
X is O, NR$^4$, CR$^4$R$^5$, where R$^4$ and R$^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl;
Y is O or S,
Z is a substituted aryl ring, having the following structure:

wherein R$^6$ and R$^7$ are independently selected from the group consisting of alkyl and may include from 1 to 10 carbons, and may be cyclic or branched chain alkyl having 3 to 10 carbons, methoxy, hydroxyl, halogen, nitrile, and trifluoromethyl; and
E is N or CR;
or, wherein:
R$^1$, R$^2$ and R$^3$ are independently H, halogen, methyl, or isopropyl;
X is NR$^4$;
R$^4$ is H;
Y is O;
R$^6$ and R$^7$ are independently H or chloro;
E is N or CR; and
R is H.

In another embodiment, the S1PR2 inhibitor is a small molecule selected from the group consisting of: N-(3,5-dichlorophenyl)-2-(4-methyl-1,8-naphthyridin-2-yl)hydrazinecarboxamide; N-(3,5-dichlorophenyl)-2-(4-isopropyl-1,8-naphthyridin-2-yl)hydrazinecarboxamide; N-(3,5-dichlorophenyl)-2-(4-isopropyl-5,8-dimethylquinolin-2-yl)hydrazinecarboxamide; N-(3,5-dichlorophenyl)-2-(4-isopropylquinolin-2-yl)hydrazinecarboxamide; N-(2,6-dichloropyridin-4-yl)-2-(4,8-dimethylquinolin-2-yl)hydrazinecarboxamide; N-(3,5-dichlorophenyl)-2-(4,8-dimethylquinolin-2-yl)hydrazinecarboxamide; N-(2,6-dichloropyridin-4-yl)-2-(4-methylquinolin-2-yl)

hydrazinecarboxamide; and N-(3,5-dichlorophenyl)-2-(4,5,8-trimethylquinolin-2-yl)hydrazinecarboxamide.

In another embodiment, the S1PR2 inhibitor is a compound with the general formula:

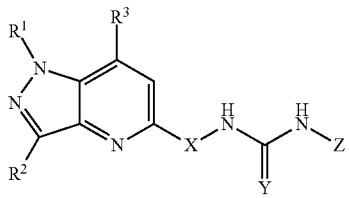

Formula III wherein:
$R^1$ $R^2$ are independently selected from the group consisting of H and alkyl, methoxy, hydroxyl, halogen, nitrile, and trifluoromethyl;
$R^3$ is independently selected from the group consisting of alkyl, methoxy, hydroxyl, halogen, nitrile, and trifluoromethyl;
X is O, $NR^4$, $CR^4R^5$, where $R^4$ and $R^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl;
Y is O or S;
R is H, methoxy or alkyl;
Z is a substituted aryl ring, having the following structure:

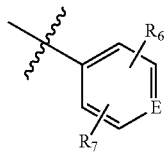

wherein $R^6$ and $R^7$ are independently selected from the group consisting of alkyl and may include from 1 to 10 carbons, and may be cyclic or branched chain alkyl having 3 to 10 carbons, methoxy, ethoxy, propoxy, butoxy, hydroxyl, halogen, nitrile, and trifluoromethyl; and E is N or CR;
or wherein:
$R^1$, $R^2$ and $R^3$ are independently methyl or isopropyl;
X is $NR^4$ or $CR^4R^5$;
$R^4$ is H;
$R^5$ is H;
Y is O;
$R^6$ and $R^7$ are independently selected from the group consisting of alkyl and may include from 1 to 5 carbons, methoxy, ethoxy, propoxy, butoxy, chloro and trifluoromethyl;
E is N or CR; and
R is H or methoxy.

In another embodiment, the S1PR2 inhibitor is a small molecule selected from the group consisting of: N-(3,5-dichlorophenyl)-2-(7-isopropyl-1,3-dimethyl-1H-pyrazolo[4,3-b]pyridin-5-yl)hydrazinecarboxamide; 1-(2,6-dichloropyridin-4-yl)-3-((7-isopropyl-1,3-dimethyl-1H-pyrazolo[4,3-b]pyridin-5-yl)methyl)urea; N-(2-butyl-6-chloropyridin-4-yl)-2-(7-isopropyl-1,3-dimethyl-1H-pyrazolo[4,3-b]pyridin-5-yl)hydrazinecarboxamide; N-(2-chloro-6-ethoxypyridin-4-yl)-2-(7-isopropyl-1,3-dimethyl-1H-pyrazolo[4,3-b]pyridin-5-yl)hydrazinecarboxamide; 1-(3,5-dichlorophenyl)-3-((1,3,7-trimethyl-1H-pyrazolo[4,3-b]pyridin-5-yl)methyl)urea; N-(2,6-dichloropyridin-4-yl)-2-(7-isopropyl-1,3-dimethyl-1H-pyrazolo[4,3-b]pyridin-5-yl)hydrazinecarboxamide; N-(3,5-bis(trifluoromethyl)phenyl)-2-(7-isopropyl-1,3-dimethyl-1H-pyrazolo[4,3-b]pyridin-5-yl)hydrazinecarboxamide; N-(3-chloro-5-methoxypyridin-4-yl)-2-(7-isopropyl-1,3-dimethyl-1H-pyrazolo[4,3-b]pyridin-5-yl)hydrazinecarboxamide; 1-(2,6-dichlorophenyl)-3-((7-isopropyl-1,3-dimethyl-1H-pyrazolo[4,3-b]pyridin-5-yl)methyl)urea; 1-(2-chloro-6-methoxypyridin-4-yl)-3-((7-isopropyl-1,3-dimethyl-1H-pyrazolo[4,3-b]pyridin-5-yl)methyl)urea; N-(2-chloro-6-propylpyridin-4-yl)-2-(7-isopropyl-1,3-dimethyl-1H-pyrazolo[4,3-b]pyridin-5-yl)hydrazinecarboxamide; 1-(2-chloro-6-propylpyridin-4-yl)-3-((7-isopropyl-1,3-dimethyl-1H-pyrazolo[4,3-b]pyridin-5-yl)methyl)urea; 1-(2-chloro-6 ethoxypyridin-4-yl)-3-((7-isopropyl-1,3-dimethyl-1H-pyrazolo[4,3-b]pyridin-5-yl)methyl)urea; 1-(2-chloro-6-propoxypyridin-4-yl)-3-((7-isopropyl-1,3-dimethyl-1H-pyrazolo[4,3-b]pyridin-5-yl)methyl)urea; N-(2-chloro-6-propoxypyridin-4-yl)-2-(7-isopropyl-1,3-dimethyl-1H-pyrazolo[4,3-b]pyridin-5-yl)hydrazinecarboxamide; N-(2-butoxy-6-chloropyridin-4-yl)-2-(7-isopropyl-1,3-dimethyl-1H-pyrazolo[4,3-b]pyridin-5-yl)hydrazinecarboxamide; 1-(2-butoxy-6-chloropyridin-4-yl)-3-((7-isopropyl-1,3-dimethyl-1H-pyrazolo[4,3-b]pyridin-5-yl)methyl)urea; N-(2-ethoxypyridin-4-yl)-2-(7-isopropyl-1,3-dimethyl-1H-pyrazolo[4,3-b]pyridin-5-yl)hydrazinecarboxamide; and N-(5-chloro-2,4-dimethoxyphenyl)-2-(7-isopropyl-1,3-dimethyl-1H-pyrazolo[4,3-b]pyridin-5-yl)hydrazinecarboxamide.

Administration

Any suitable method of administering a composition as described herein to a subject may be used. In these methods, the compositions can be administered to a subject by any suitable route, e.g., systemically by intravenous injection, directly through intraocular injection, orally, etc. The compositions may be administered directly to a target site by, for example, surgical delivery to an internal or external target site, or by catheter to a site accessible by a blood vessel. For example, in a method of treating FEVR, a composition as described herein may be delivered through intraocular injection, orally, or intravenously. The compositions may be administered in a single bolus, multiple injections, or by continuous infusion (e.g., intravenously, or interathecally by peritoneal dialysis, pump infusion). For parenteral administration, the compositions are preferably formulated in a sterilized pyrogen-free form. As indicated above, the compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like. The compositions described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions.

The therapeutic methods described herein in general include administration of a therapeutically effective amount of the compositions described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The methods and compositions herein may be used in the treatment of any other disorders or diseases relating to anemia.

Effective Doses

The compositions described herein are preferably administered to a mammal (e.g., human) in an effective amount, that is, an amount capable of producing a desirable result in a treated mammal (e.g., treating FEVR or ROP through administration of S1PR2 inhibitors). Such a therapeutically effective amount can be determined according to standard methods.

Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition as described herein may be determined based on preclinical efficacy and safety.

EXAMPLES

The present invention is further illustrated by the following specific examples. The examples are provided for illustration only and should not be construed as limiting the scope of the invention in any way.

Figure 6:
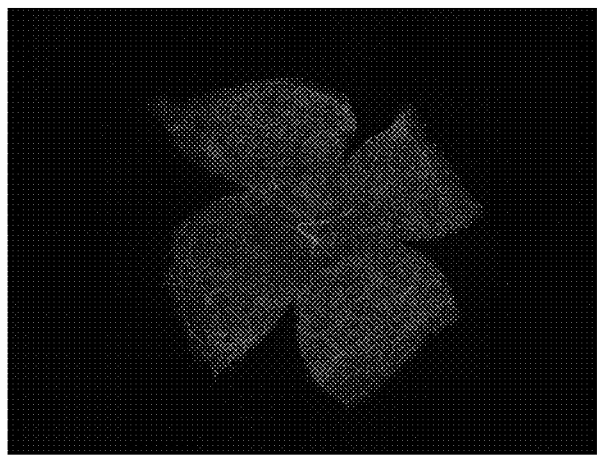
FIG. 6 illustrates the restoration of normal vasculature patterning in the Tspan12$^{-/-}$ mouse model of FEVR upon inactivation of the S1pr2 gene. Retinas were flat mounted at P17 and the vasculature visualized by confocal microscopy subsequent to staining with iso-lectin B4 AlexaFluor 594. Similar results were observed for Fzd4$^{-/-}$ S1pr2$^{-/-}$ mice.
Figure 6:
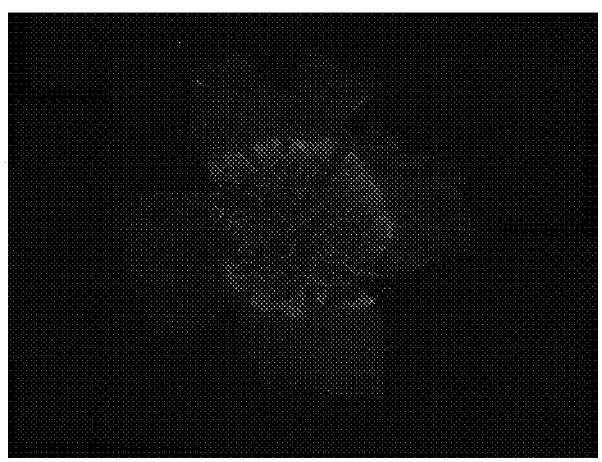
Figure 6:
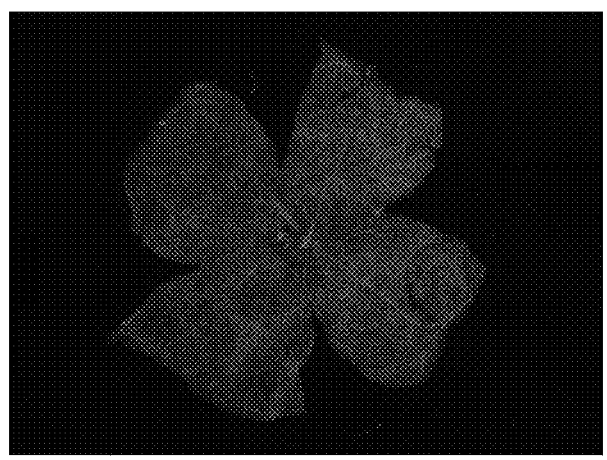

The inhibition of S1PR2 signaling ameliorates the defects in vascular development observed in FEVR and ROP as S1P plays a critical role in retinal vasculature development. For instance, the administration, through intraocular injection, of a monoclonal antibody to S1P that binds and inactivates this lipid, to mice subjected to laser induced choroidal neovascularization significantly enhances normal retinal revascularization. Moreover, S1P2 is strongly induced in endothelial cells during hypoxic stress, suggesting that S1P signals through S1PR2 to produce the abnormal vasculature observed in ROP. Additionally, neonatal S1pr2$^{-/-}$ mice subjected to the ROP model display a decrease in pathologic neovascularization, endothelial gaps, and inflammatory cell infiltration. Lastly, post-natal inactivation of the S1PR1 in mice results in abnormal retinal vasculature, consistent with S1PR1 and S1PR2 acting in opposition to regulate retinal vascular development. S1pr2$^{-/-}$ Tspan12$^{-/-}$ double knockout mice were generated and observed a remarkable restoration of retinal vasculature patterning was observed that resembled wild type mice (FIG. 6). Fzd4$^{-/-}$ S1pr2$^{-/-}$ mice were also generated and these mice also show restoration of retinal vasculature patterning. Thus, inhibition of S1PR2 is a significant therapeutic approach for diseases such as FEVR and ROP.

Computer Aided Drug Design of S1PR2 Antagonists

In general, G protein coupled receptors are considered highly druggable, and a broad specificity S1PR agonist (Fingolimod, trade name Gilenya) that simultaneously targets S1PR1-3 and -5 is on the market for the treatment of multiple sclerosis. Computer aided drug design has been used in the past to successfully design and synthesize small molecule inhibitors of lipid enzymes that are now in late stage preclinical evaluation for a subsequent Phase 1/2a clinical trial. A similar developmental path forward for the design and testing of S1PR2 antagonists can be employed.

Figure 7:
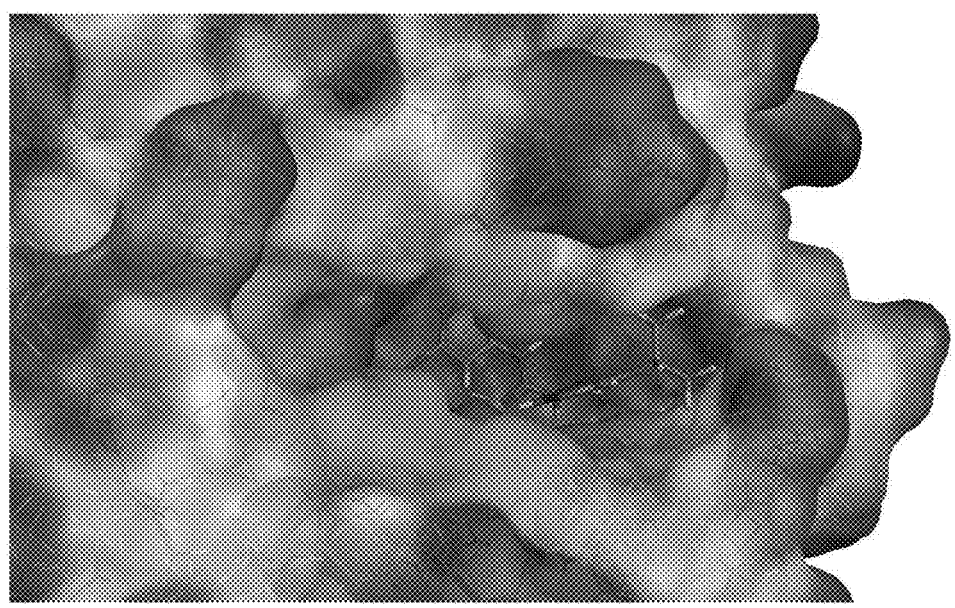
FIG. 7 illustrates the sphingosine-1-phosphate receptor 2 (S1PR2) binding pocket. The human S1PR2 ligand binding pocket is shown with JTE-103 bound. JTE-103 is a tool compound (uM affinity) with 10-fold greater specificity for S1PR2 versus other S1PRs. Molecular modeling of the S1PR2 binding pocket was used to identify potential potent S1PR2 inhibitors.

To identify inhibitors of S1PR2 by computational means, the Molecular Operating Environment (MOE) program was used to perform modeling on the S1PR1 structure. Throughout the process, the CHARMM27 force field was implemented and a gas phase environment was specified. The amino acid sequence of S1PR2 was obtained from the UniProt archive. The amino acid sequences of S1PR2 and S1PR1 were aligned, and a homology model was generated from the alignment. The generated model was protonated for a temperature of 310K, a pH of 7.0, and a salt concentration of 0.1 mol/L. The site finder tool in MOE was used to identify the binding pocket of the receptor. A pocket composed of 34 amino acids located on the extracellular face of the protein was identified, and correlates to that of its counterpart S1PRs (FIG. 7).

Figure 8:
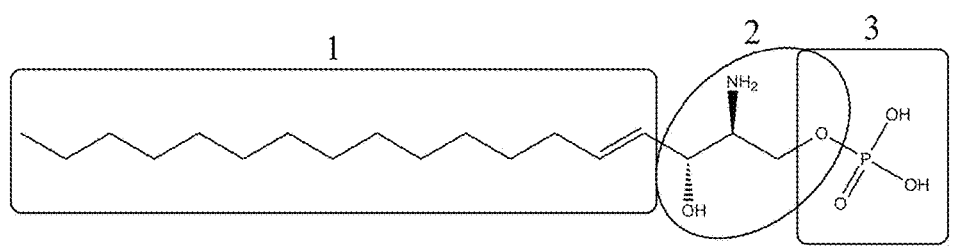
FIG. 8 illustrates the sphingosine-1-phosphate and its identified target regions. These identified compounds interact with the binding pocket more strongly than its known receptor, and thus prevent S1P from binding. The identified compounds are available for purchase. The following 21 (as identified by their PubChem identification (a combination of natural products, drugs and known chemical entities) were selected as viable targets for in vitro and in vivo testing. PubChem identifiers are: 3382778; 44317142 (also as 520 and 644260); 54736865; 3866342; 46891770 (also as 3247041); 51624406; 9578291; 9864156; 365015; 28094480; 40592676; 10883396; 342302; 56923845; 54734912; 18390590; 56923928; 51508548; 28960354; 51624683; 27993.

The main ligand of the S1PR2 receptor, S1P, has three distinct chemical regions. These regions (FIG. 8) were used to search the PubChem database for similar molecules containing either region 1, 2 or 3. As well, sulfate groups were also included in the search as they are bioisosteres of phosphate. Compounds were identified based on the following criteria: they must have a molecular weight less than 390, an XLogP value between −1 and 7 for regions 2 and 3, or an XLogP value less than 5 and a total polar surface area from 35-120 for region 1. The compounds identified from each region were imported into MOE as a database. A total of 62,125 results were obtained for region 1; 2,971 for region 2, and; 13,442 for region 3. These molecules were first washed to remove any salt ions that may have been included in the structure, and were energy optimized using the CHARMM27 force field in a gas phase environment. The compounds were then submitted to a virtual screen through the identified binding pocket on S1PR2.

From the results of the virtual screen, the best 100 compounds for each region were selected and subjected to a more rigorous method of docking: induced fit versus S1PR2 and S1PR1. This docking allows for the amino acid side chains lining the pocket to move, as well as the ligand being docked. The resulting databases were examined for compounds with an S score that was better than the score of S1P, and have predicted specific for S1PR2 versus S1PR1. The identified compounds were then screened for availability to purchase and 21 (FIG. 8) were found to be commercially available and were selected as viable targets for testing. Their PubChem identification was the following: 3382778; 44317142 (also as 520 and 644260); 54736865; 3866342; 46891770 (also as 3247041); 51624406; 9578291; 9864156;

365015; 28094480; 40592676; 10883396; 342302; 56923845; 54734912; 18390590; 56923928; 51508548; 28960354; 51624683; 27993. Their efficacy can readily be compared to the tool compound JTE-103, a low affinity S1PR inhibitor with some specificity for S1PR2.

Confirmation of by S1PR2 Antagonists in Zebrafish and Mouse Models of FEVR

Figure 9:
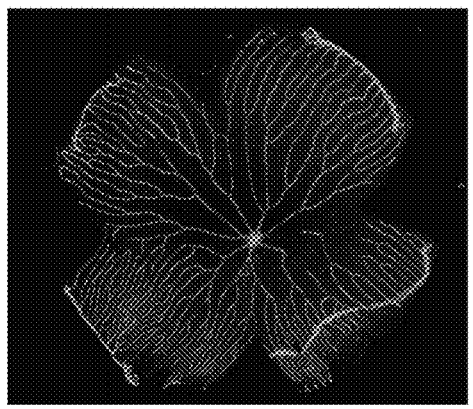
FIG. 9 illustrates that inactivation of the fzd4 gene in adult zebrafish results in the aberrant neovascularization observed in humans and mice. To target the fzd4 gene, a pair of TALEN nucleases was created. The founders carrying a significant proportion of the mutation were mated to fli1: EGFP transgenic fish (GFP marker for vasculature) and the resulting F1 fish were grown to adulthood. An insertion of 10 nucleotides was confirmed in the open reading frame of the fzd4 gene. Pairs of fzd4 heterozygous fish were mated to produce progeny containing homozygous mutants. Homozygous mutant fish did not have any apparent embryonic phenotype and were grown to adulthood. To check if the retinal vasculature is affected by the fzd4 mutation, retinas were dissected and flat mounted from wild-type and mutant fish and were visualized by confocal microscopy. The homozygous fzd4$^{-/-}$ mutants have a large area of avascularity and an abnormal vascular pattern in the vascularized areas.
Figure 9:
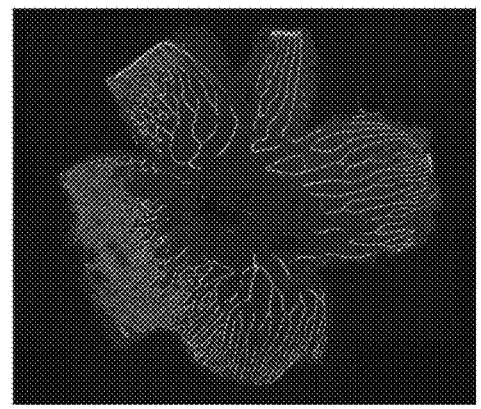

Knockout approaches permit the generation of zebrafish models that recapitulate human diseases, allowing for a rapid intermediate in vivo step for drug screening prior to more time consuming and expensive mammalian studies. The S1PR2 drug target and the FZD4 pathway are highly conserved between zebrafish and humans. The TALEN system was used to generate germ line fzd4$^{-/-}$ zebrafish (FIG. 9) (morpholinos have been used versus the s1pr2 to confirm its inhibition also restores normal vasculature in this model).

To assay the identified S1PR2 inhibitors as well as the known tool compound JTE-103, three fzd4$^{-/-}$ zebrafish embryos are arrayed in 96-well plates. At 24 hours post-fertilization (hpf) compounds are then transferred to the embryo plate at final concentrations of 1-30 μM. Embryos are then incubated with compounds at 28.5° C. for 12 h and screened for gross global developmental effects. At various time frames (2-12 days) embryos are then overdosed with Tricaine (MS-222) and fixed in 4% paraformaldehyde and their retinal vasculature can be determined. Those compounds that best restore normal vasculature to zebrafish are subsequently tested in the Tspan12$^{-/-}$ and Fzd4$^{-/-}$ mice to isolate the most effective therapeutic compounds.

For work in mice, compounds are delivered by intraocular injection to the eye (1-30 μM) of mice at P7, P10, P17, and P28 (8-12 mice per compound for 5 doses of each compound). This time frame determines at what stage FEVR can be effectively treated by a S1PR2 antagonist. Retinal phenotypes and ocular function are then determined as described above for the study of the s1pr2$^{-/-}$tspan12$^{-/-}$ and s1pr2$^{-/-}$fzd4$^{-/-}$ mice.

The invention claimed is:

1. A method of treating familial exudative vitreoretinopathy in a patient in need thereof, comprising administering to the patient a pharmaceutical composition comprising a therapeutically effective amount of a compound of formula (II):

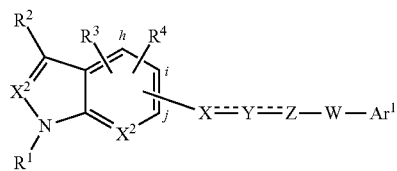

Formula II wherein,
Ar$^1$ is pyridine, which is optionally substituted;
W is —NR$^a$—, wherein R$^a$ is independently selected from hydrogen and C$_1$-C$_3$ alkyl;

Z is C(=O)—;
Y is —NR$^a$—, wherein R$^a$ is independently selected from hydrogen and C$_1$-C$_3$ alkyl;
X is —CH$_2$—;
R$^1$ is C$_1$-C$_{12}$ alkyl;
R$^2$, R$^3$, and R$^4$ are each independently hydrogen, halogen, C$_1$-C$_6$ alkyl, C$_1$-C$_4$ alkoxy, C$_1$-C$_6$ perhaloalkyl, C$_1$-C$_4$ perhaloalkoxy, amino, mono- or di-C$_1$-C$_4$ alkylamino, C$_3$-C$_7$ cycloalkyl, or C$_3$-C$_7$ cycloalkyloxy, wherein R$^3$ and R$^4$ can be positioned at h, i, or j, but not simultaneously at the same position; and
X$^2$ in both cases is N.

2. The method of claim 1, wherein the compound is

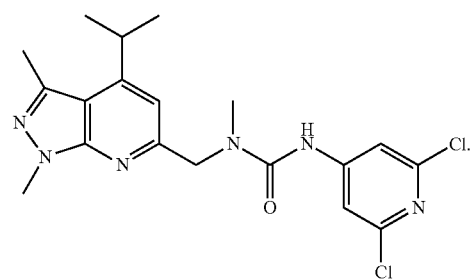 [SMILES: Cc1nn(C)c2nc(CN(C)C(=O)Nc3cc(Cl)nc(Cl)c3)cc(C(C)C)c12]

3. The method of claim 1, wherein the compound is

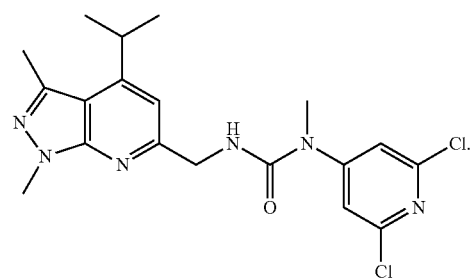 [SMILES: Cc1nn(C)c2nc(CNC(=O)N(C)c3cc(Cl)nc(Cl)c3)cc(C(C)C)c12]

4. The method of claim 1, wherein the compound is

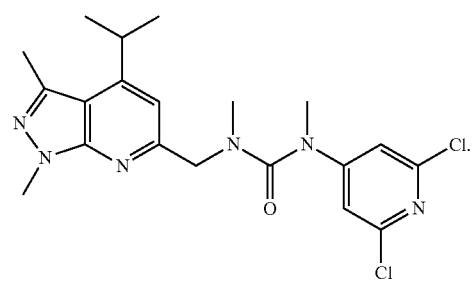 [SMILES: Cc1nn(C)c2nc(CN(C)C(=O)N(C)c3cc(Cl)nc(Cl)c3)cc(C(C)C)c12]

* * * * *